United States Patent
Scott

(10) Patent No.: US 11,382,269 B2
(45) Date of Patent: Jul. 12, 2022

(54) APPARATUS FOR HARVESTING CANNABIS/HEMP MATERIALS

(71) Applicant: Bryan Scott, Seaside, CA (US)

(72) Inventor: Bryan Scott, Seaside, CA (US)

( * ) Notice: Subject to any disclaimer, the term of this patent is extended or adjusted under 35 U.S.C. 154(b) by 341 days.

(21) Appl. No.: 16/807,149

(22) Filed: Mar. 2, 2020

(65) Prior Publication Data
US 2021/0267124 A1   Sep. 2, 2021

(51) Int. Cl.
| | |
|---|---|
| A01F 29/01 | (2006.01) |
| A01D 45/06 | (2006.01) |
| A01F 29/10 | (2006.01) |
| A01F 29/06 | (2006.01) |
| B02C 17/02 | (2006.01) |
| A01G 3/00 | (2006.01) |
| A23N 15/06 | (2006.01) |

(Continued)

(52) U.S. Cl.
CPC ............ *A01D 45/065* (2013.01); *A01F 29/01* (2013.01); *A01F 29/06* (2013.01); *A01F 29/10* (2013.01); *A01G 3/00* (2013.01); *A01G 3/002* (2013.01); *A23N 15/06* (2013.01); *A24B 3/07* (2013.01); *A61K 2236/15* (2013.01); *B02C 17/02* (2013.01); *B02C 21/02* (2013.01); *B02C 23/10* (2013.01); *B02C 23/16* (2013.01); *B02C 25/00* (2013.01)

(58) Field of Classification Search
CPC . A01G 3/00; A01G 3/002; A24B 3/07; A01D 45/065; A01D 61/008; A01D 67/04; A01F 29/01; A01F 29/06; A01F 29/10; A01F 11/02; A23N 15/06; A61K 2236/15; B02C 17/02; B02C 21/02; B02C 23/10; B02C 23/16; B02C 25/00
See application file for complete search history.

(56) References Cited

U.S. PATENT DOCUMENTS

| | | | |
|---|---|---|---|
| 1,598,419 A * | 8/1926 | Bonaventura | B07B 1/18 209/394 |
| 2,316,986 A * | 4/1943 | Parker | B07B 1/50 209/384 |

(Continued)

FOREIGN PATENT DOCUMENTS

| | | | | |
|---|---|---|---|---|
| CA | 3018055 A1 * | 3/2019 | | A01D 45/065 |
| DE | 102020200761 A1 * | 7/2021 | | A01D 45/06 |

(Continued)

*Primary Examiner* — Arpad Fabian-Kovacs
(74) *Attorney, Agent, or Firm* — Patent Ingenuity, P.C.; Samuel K. Simpson

(57) ABSTRACT

An apparatus has a trailer with one or more wheels and a connector that connects the trailer to an automotive machine that mobilizes the trailer from a first position to a second position within a field of one or more plants. Further, the apparatus has a branch trimming device operably positioned on the trailer. Additionally, the apparatus has a conveyer belt operably positioned on the trailer. The conveyer belt receives a trimmed plant that has one or more branches trimmed off by the branch trimming device. The apparatus also has one more cutting devices. Finally, the apparatus has a tumbler that receives the trimmed plant from the conveyer belt and rotates with respect to the one or more cutting devices to cut the trimmed plant into the one or more buds. A bottom portion of the tumbler is positioned in proximity to the one or more cutting devices.

11 Claims, 11 Drawing Sheets

(51) Int. Cl.
    *B02C 25/00*     (2006.01)
    *A24B 3/07*     (2006.01)
    *B02C 21/02*     (2006.01)
    *B02C 23/16*     (2006.01)
    *B02C 23/10*     (2006.01)

(56) References Cited

U.S. PATENT DOCUMENTS

| | | | | |
|---|---|---|---|---|
| 3,729,096 | A * | 4/1973 | Fitzner | B07B 1/22 209/406 |
| 4,240,589 | A * | 12/1980 | Martin | B07B 1/4681 209/44.3 |
| 4,736,574 | A * | 4/1988 | Walker | A01D 46/243 56/328.1 |
| 6,305,552 | B1 * | 10/2001 | Coleman | B07B 1/24 209/664 |
| 6,443,234 | B1 * | 9/2002 | Raymond | A01D 23/04 171/42 |
| 7,080,741 | B1 * | 7/2006 | Butzin | B07B 1/24 209/664 |
| 8,678,195 | B2 * | 3/2014 | Azzolin | E02F 7/06 209/252 |
| 9,161,566 | B2 * | 10/2015 | Hall | A23N 15/06 |
| 9,380,805 | B2 * | 7/2016 | Holcomb | A23N 15/12 |
| 9,913,427 | B2 * | 3/2018 | de Lorimier | A01D 45/26 |
| 2017/0001200 | A1 * | 1/2017 | Leffel | A61K 36/185 |
| 2019/0246568 | A1 * | 8/2019 | Seidel | A01G 3/00 |
| 2021/0368680 | A1 * | 12/2021 | Wisdom | A01D 46/30 |

FOREIGN PATENT DOCUMENTS

| | | | | |
|---|---|---|---|---|
| EP | 1643825 | B1 * | 9/2007 | A01D 45/065 |
| EP | 3677110 | A1 * | 7/2020 | A01D 45/065 |
| FR | 2872675 | A1 * | 1/2006 | A01B 75/00 |
| WO | WO-2005082175 | A1 * | 9/2005 | A01D 45/065 |
| WO | WO-2021067418 | A1 * | 4/2021 | A01D 45/16 |

* cited by examiner

APPARATUS FOR HARVESTING CANNABIS/HEMP MATERIALS

BACKGROUND

1. Field

This disclosure generally relates to cannabis plants. More particularly, the disclosure relates to the field of harvesting cannabis plants.

2. General Background

In contrast with many types of plants that are harvested, much of a cannabis plant may be put to use. Although the buds (also known as "flowers") of the cannabis plant are the portions typically thought of as being used for consumption, the remaining parts (referred to as "biomass"), such as the stalk and leaves, may be used for a variety of purposes (including, but not limited to, clothing, oils, and teas).

Yet, conventional harvesting configurations are most concerned with preservation of only a portion of the cannabis plant, typically the biomass. For example, a conventional harvesting configuration may use a combine, which is typically used to harvest corn, for harvesting biomass. As a result, such configurations may harvest the biomass, at the expense of damaging the cannabis buds.

Given the potential uses of cannabis buds, current harvesting configurations do not efficiently and effectively harvest cannabis buds.

SUMMARY

An apparatus has a trailer with one or more wheels and a connector that connects the trailer to an automotive machine that mobilizes the trailer from a first position to a second position within a field of one or more plants. Further, the apparatus has a branch trimming device operably positioned on the trailer. Additionally, the apparatus has a conveyer belt operably positioned on the trailer. The conveyer belt receives a trimmed plant that has one or more branches trimmed off by the branch trimming device. The apparatus also has one more cutting devices. Finally, the apparatus has a tumbler that receives the trimmed plant from the conveyer belt and rotates with respect to the one or more cutting devices to cut the trimmed plant into the one or more buds. A bottom portion of the tumbler is positioned in proximity to the one or more cutting devices.

Furthermore, a process trims, with a branch trimming device operably positioned at a trailer, one or more branches from a plant to form a trimmed plant. The trailer has one or more wheels and a connector that connects the trailer to an automotive machine that mobilizes the trailer from a first position to a second position within a field of one or more plants. The process also receives, via a conveyer belt operably positioned on the trailer, the trimmed plant. Moreover, the process sends, via the conveyer belt, the trimmed plant to a tumbler. In addition, the process rotates, via the tumbler, the trimmed plant with respect to the one or more cutting devices to cut the trimmed plant into the one or more buds, wherein a bottom portion of the tumbler is positioned in proximity to the one or more cutting devices.

BRIEF DESCRIPTION OF THE DRAWINGS

The above-mentioned features of the present disclosure will become more apparent with reference to the following description taken in conjunction with the accompanying drawings wherein like reference numerals denote like elements and in which.

DETAILED DESCRIPTION

An apparatus and process are provided for harvesting various cannabis/hemp materials (e.g., buds, leaves, and/or stalks). In particular, the apparatus and process effectively and efficiently divide a cannabis plant into its constituent parts so that the entirety of the cannabis plant can be optimally preserved and utilized.

Figure 1A:
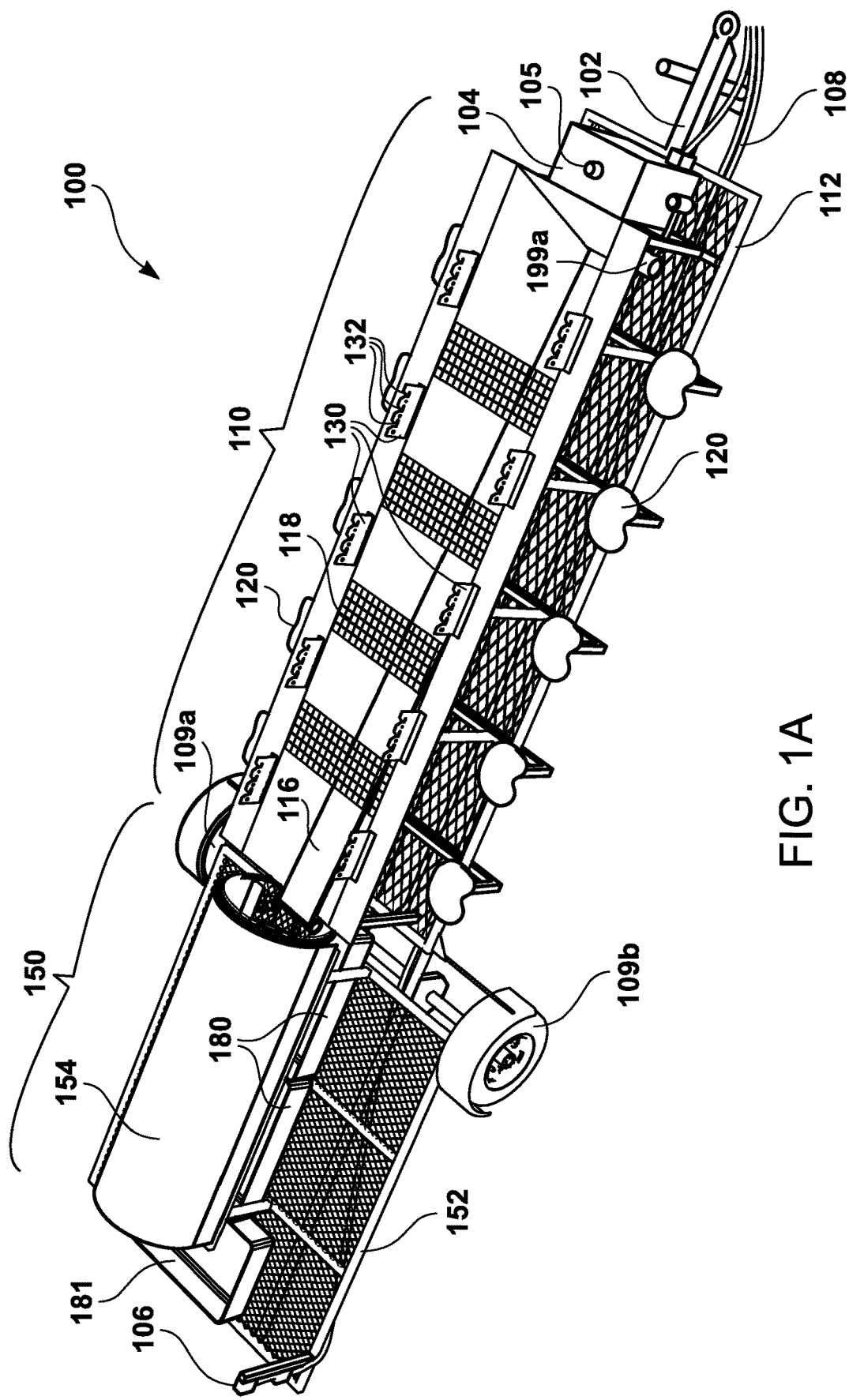
FIG. 1A illustrates a top perspective view of the harvesting trailer apparatus.
Figure 1B:
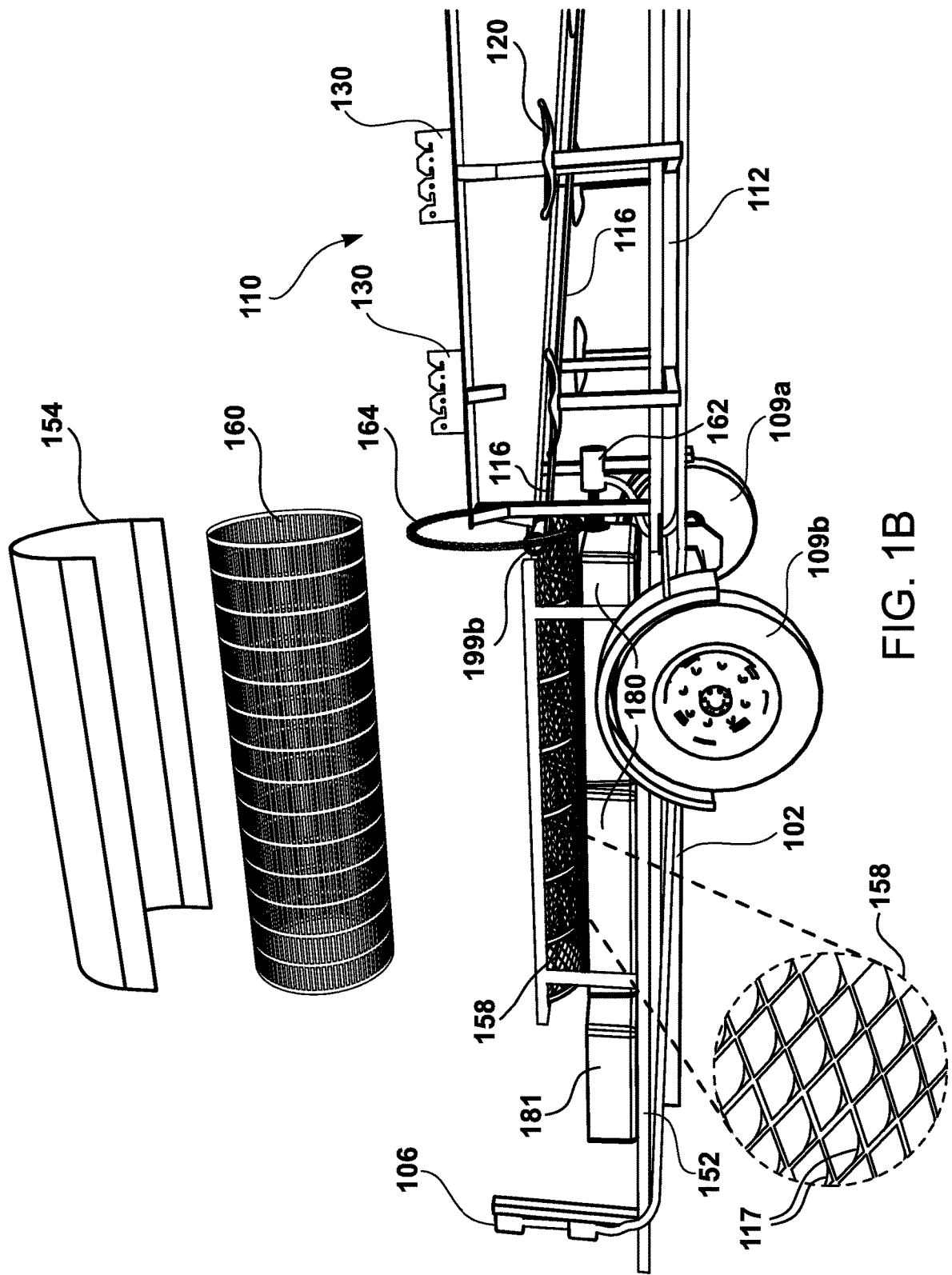
FIG. 1B illustrates a side perspective view of the tumbler apparatus illustrated in FIG. 1A.

FIGS. 1A and 1B illustrate perspective views of a harvesting trailer apparatus 100 that may be used to harvest cannabis/hemp materials. In particular, FIG. 1A illustrates a top perspective view of the harvesting trailer apparatus 100. A load-bearing connector 102 allows the harvesting trailer apparatus 100 to be connected to an automotive machine (e.g., tractor) that mobilizes the harvesting trailer apparatus 100 throughout a harvesting environment, such as a cannabis field. For example, the harvesting trailer apparatus 100 may have a first wheel 109a and a second wheel 109b that allow the harvesting trailer apparatus 100 to be pulled along a surface (e.g., ground) in the harvesting environment. (Two wheels are illustrated only for illustrative purposes; alternatively, more or less than two wheels may be utilized.)

Furthermore, the harvesting trailer apparatus 100 may have a frame 112 (e.g., mesh platform) upon which a conveyer apparatus 110 may be positioned. In particular the conveyer apparatus 110 may have a conveyer belt 116 that receives one or more cannabis/hemp materials for movement along the frame 112 toward a tumbler apparatus 150. In one embodiment, the conveyer belt 116 may be operated by a conveyer operational mechanism (e.g., hydraulic pump, motor, etc.), which may be enclosed in an operational mechanism enclosure 104. Furthermore, the conveyer operational mechanism may be in operable communication with one or more shafts (e.g., a first shaft 199a and 199b) upon which the conveyer belt 116 may rotate. The harvesting trailer apparatus 100 may also have one or more seats 120 configured for one or more human harvesters to sit during movement of the harvesting trailer apparatus 100. In essence, the human harvesters may drop cannabis/hemp materials onto the conveyer belt 116 to allow for movement of the cannabis/hemp materials along the conveyer belt 116 toward the tumbler apparatus 150. In one embodiment, the harvesting trailer apparatus 100 has a branch trimming device 130 (also known as a bucking plate) that allows the human harvesters to separate the branches of the cannabis/hemp materials from the stalks. For example, the branch trimming device 130 may have a plurality of wedges 132 that allow the one or more human harvesters to pull the cannabis/hemp materials through the branch trimming device 130 to effectively pull off the branches. The one or more human harvesters may then drop the branches, which may include the buds and leaves, onto the conveyer belt 116. The remaining stalk may or may not be stored on/in the harvesting trailer apparatus 100 (e.g., underneath the conveyer belt apparatus 110 and on top of the frame 112, potentially in a storage container situated thereon). In an alternative embodiment, the branch trimming device 130 may be a machine that automatically trims the branches upon insertion of the cannabis/hemp materials onto/into the harvesting trailer apparatus 100. Although the branch trimming device 130 is described with respect to trimming branches of the cannabis/hemp materials, it may be used, in addition or in the alternative, to trim other parts of the cannabis/hemp materials (e.g., buds, stalks, etc.).

FIG. 1B illustrates a side perspective view of the tumbler apparatus 150 illustrated in FIG. 1A. Upon receiving the cannabis/hemp materials, the tumbler apparatus 150 may rotate, via a tumbler 160, with respect to one or more cutting devices 158 to effectively separate the buds from the branches and/or leaves. In one embodiment, the tumbler 160 may be a cylindrical drum that has a plurality of openings (e.g., slits) through which leaves and/or branches may contact the one or more cutting devices 158. A tumbler operational device (e.g., motor) may be activated via a tumbler user control device 106. (The tumbler user control device 106 may activate the tumbler 160; alternatively, a conveyer belt user control device 105 may be situated on one end of the harvesting trailer apparatus 100, proximate to the to operate the conveyer belt 116, whereas the tumbler user control device 106 may be situated by the tumbler 160 to control the tumbler 160.) As an example, the cutting device 158 may be a fixed, bladed mesh frame, with one or more blades 117 integrated therein, that at least partially conforms to the shape (e.g., cylinder) of the tumbler 160. For instance, the one or more blades 117 may be positioned at one or more corners of the bladed mesh frame. Alternatively, the one or more blades 117 may be positioned at other locations within the one or more cutting devices 158. As the tumbler 160 rotates with respect to the fixed, bladed mesh frame, the leaves/branches are effectively separated from the buds. (A motor 162 or other device may be utilized to rotate the tumbler 160.) The leaves/branches may fall through the slits of the tumbler 160 into one or more leave/branch storage containers 180 situated beneath the cutting device 158 on a platform 152. (Alternatively, the storage container 180 may be an integrated storage compartment of the harvesting trailer apparatus 100.) Moreover, the remaining buds may remain in the tumbler 160 and exit out an open end of the tumbler 160 to fall into a bud storage container 181. As a result, the buds of the cannabis/hemp materials are automatically separated from the biomass of the cannabis/hemp materials.

Although the tumbler 160 is positioned as being on the same longitudinal axis as the harvesting trailer apparatus 100, it may, alternatively, be positioned on another axis, such as a transverse axis.

Various protective mechanisms/accessories may be used to protect human harvesters from getting human body parts (e.g., limbs, digits, etc.) and/or clothing caught in the moving componentry of the harvesting trailer apparatus 100, such as the tumbler apparatus 150 or the conveyer belt 116. For example, in one embodiment, a protective tumbler cover 154, optionally, may cover at least a portion of the tumbler apparatus 150 to prevent human body parts and/or clothing from getting caught in the openings of the tumbler 160 during rotation of the tumbler 160. As another example, one or more protective gratings 118 may be used to at least partially cover the conveyer apparatus 110, thereby allowing one or more human harvesters to place cannabis/hemp materials on the conveyer belt 116, while also protecting the one or more human harvesters from falling onto the conveyer belt 116. (Protective gratings 118 are provided just as an example; another type of protective covering may be used instead.)

The harvesting trailer apparatus 100 may be parked, yet the tumbler 160 may be automated such that it still rotates when the harvesting trailer apparatus 100 is parked.

Figure 2:
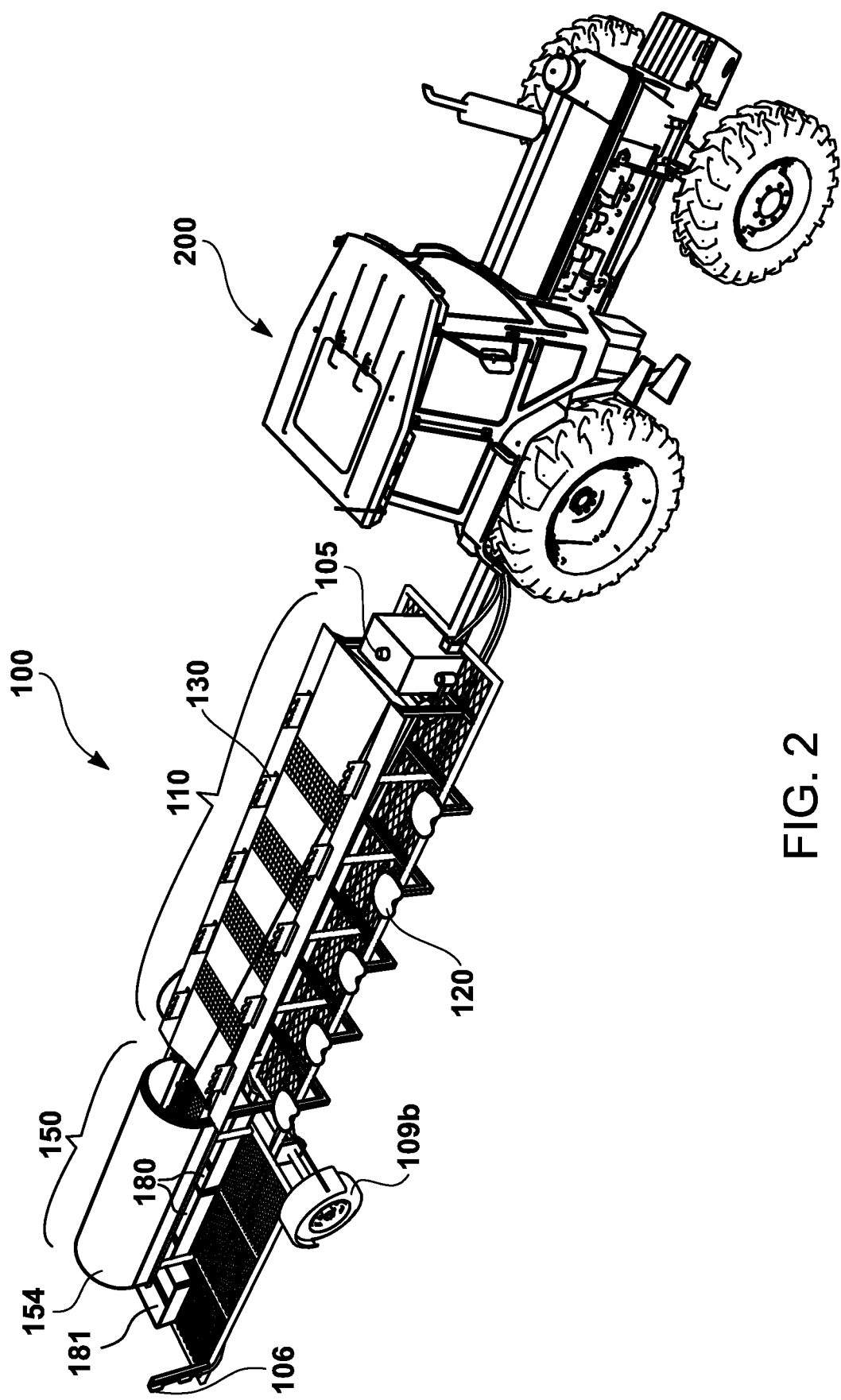
FIG. 2 illustrates a side perspective view of a tractor connected to the harvesting trailer apparatus illustrated in FIGS. 1A and 1B.

FIG. 2 illustrates a side perspective view of a tractor 200 connected to the harvesting trailer apparatus 100 illustrated in FIGS. 1A and 1B. The tractor 200, or other automotive vehicle, may be selected from a variety of vehicles. In particular, the load-bearing connector 102, illustrated in FIG. 1A, allows the harvesting trailer apparatus 100 to operate in a tractor-independent way, thereby avoiding reliance on any specific tractor to perform harvesting of cannabis/hemp materials. In essence, the load-bearing connector 102 can be customized to connect to a variety of different tractors.

Figure 3:
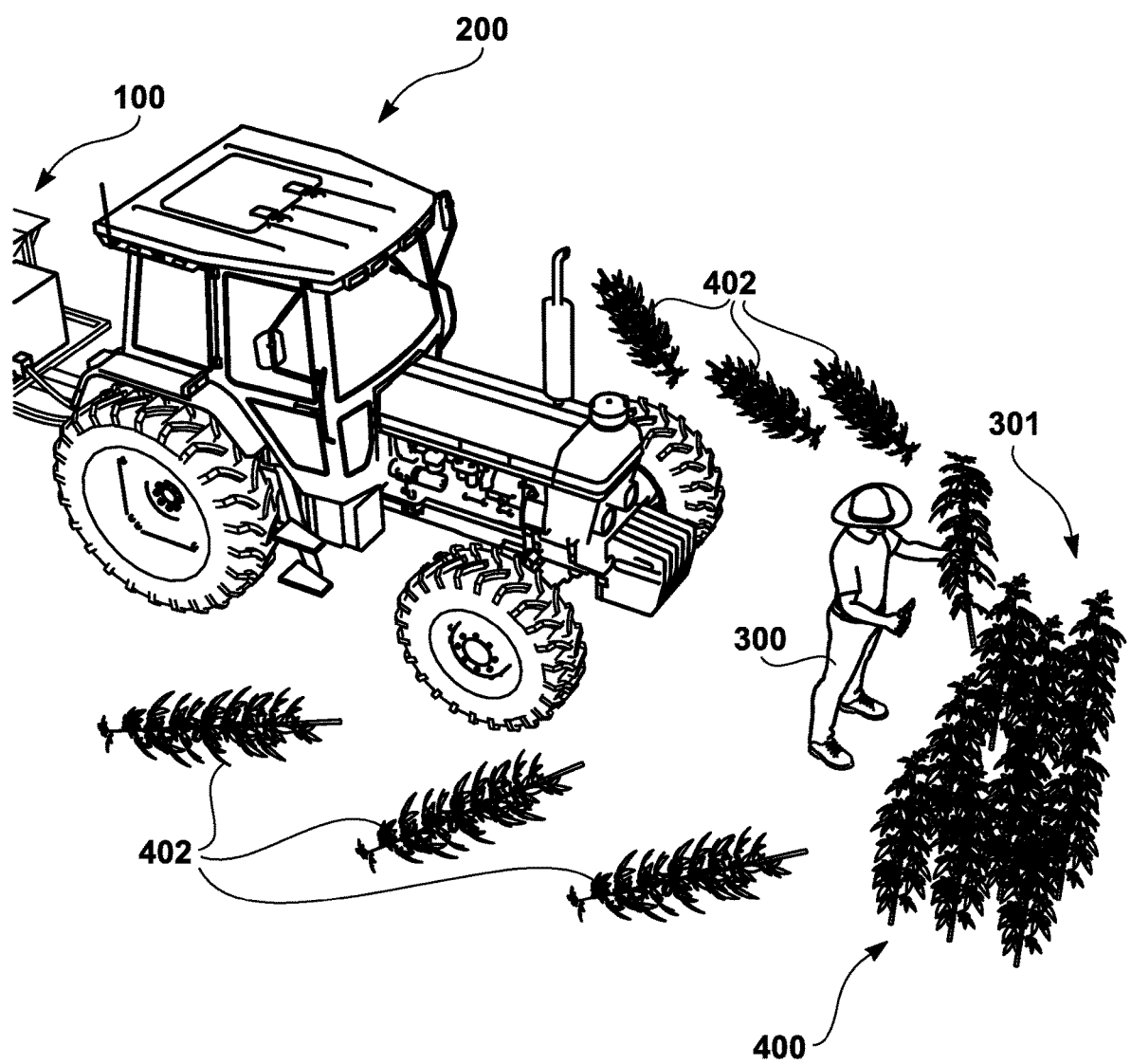
FIG. 3 illustrates the tractor, illustrated in FIG. 2, moving in conjunction with the harvesting trailer apparatus through a harvesting environment.
Figure 4:
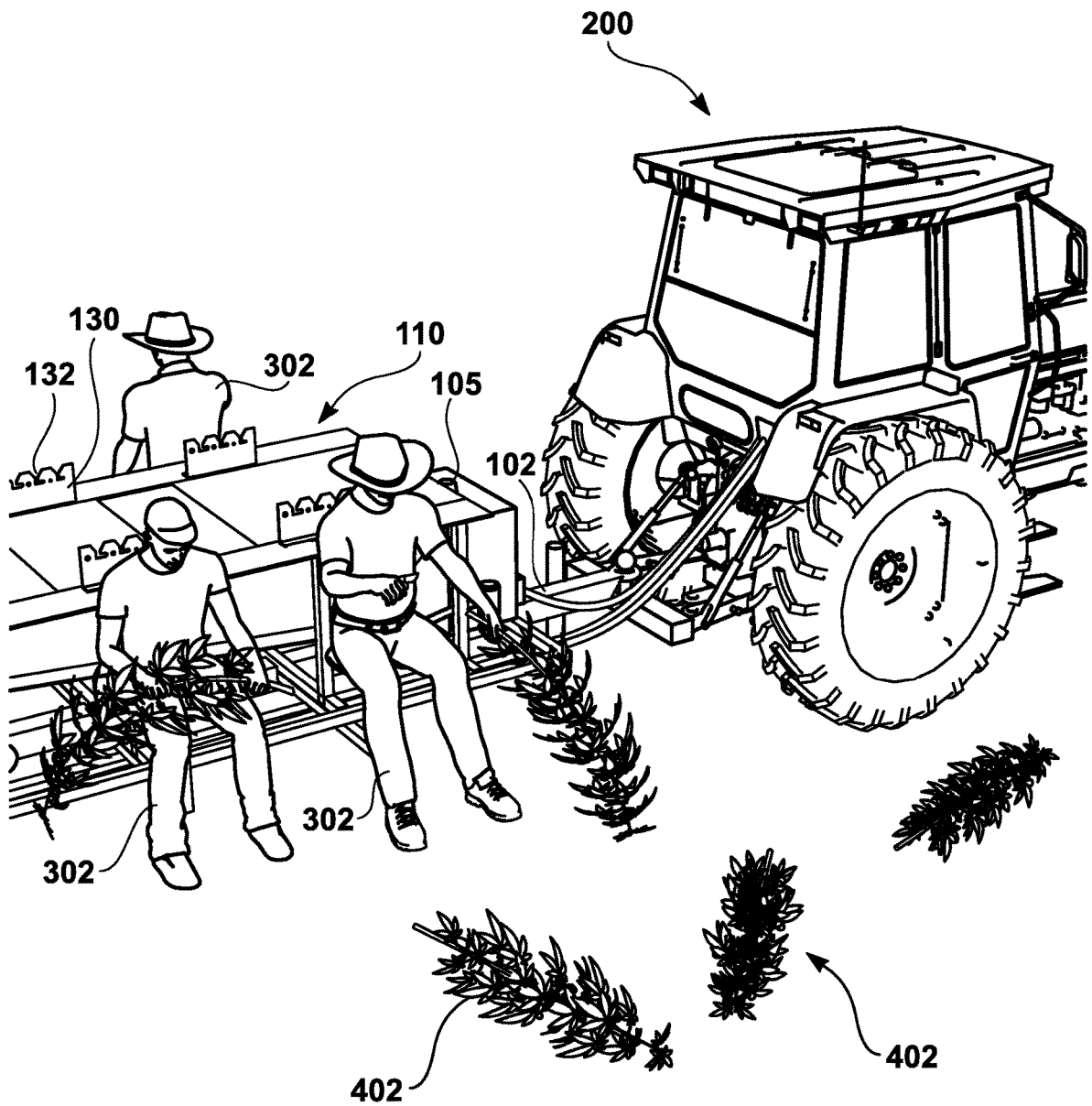
FIG. 4 illustrates a plurality of human harvesters that may be positioned on the seats to pick up the cannabis plants that were pulled by the human harvester in front of the tractor.
Figure 5:
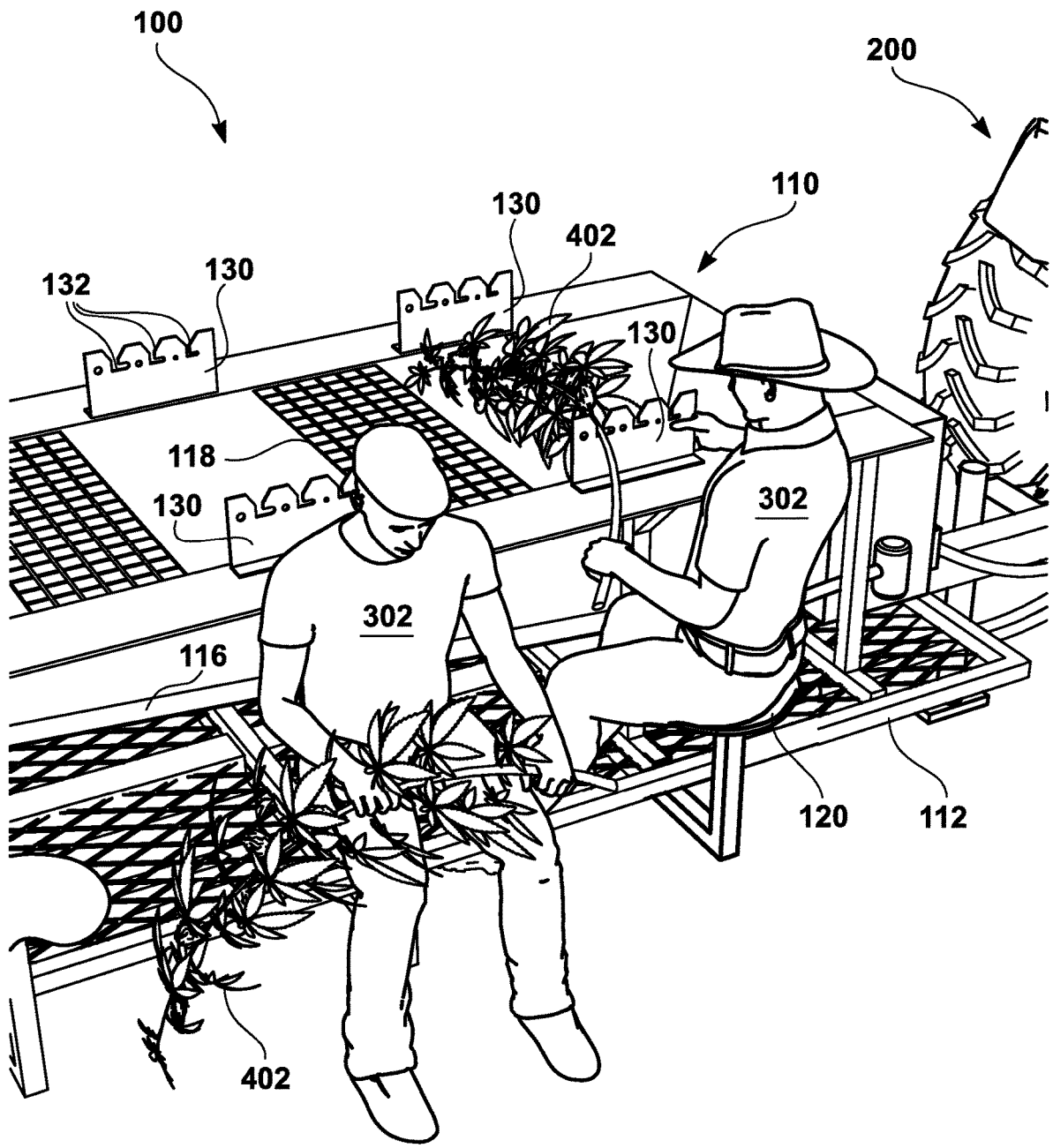
FIG. 5 illustrates the human harvesters pulling the cannabis plants through the branch trimming device to effectively pull off the branches.
Figure 6:
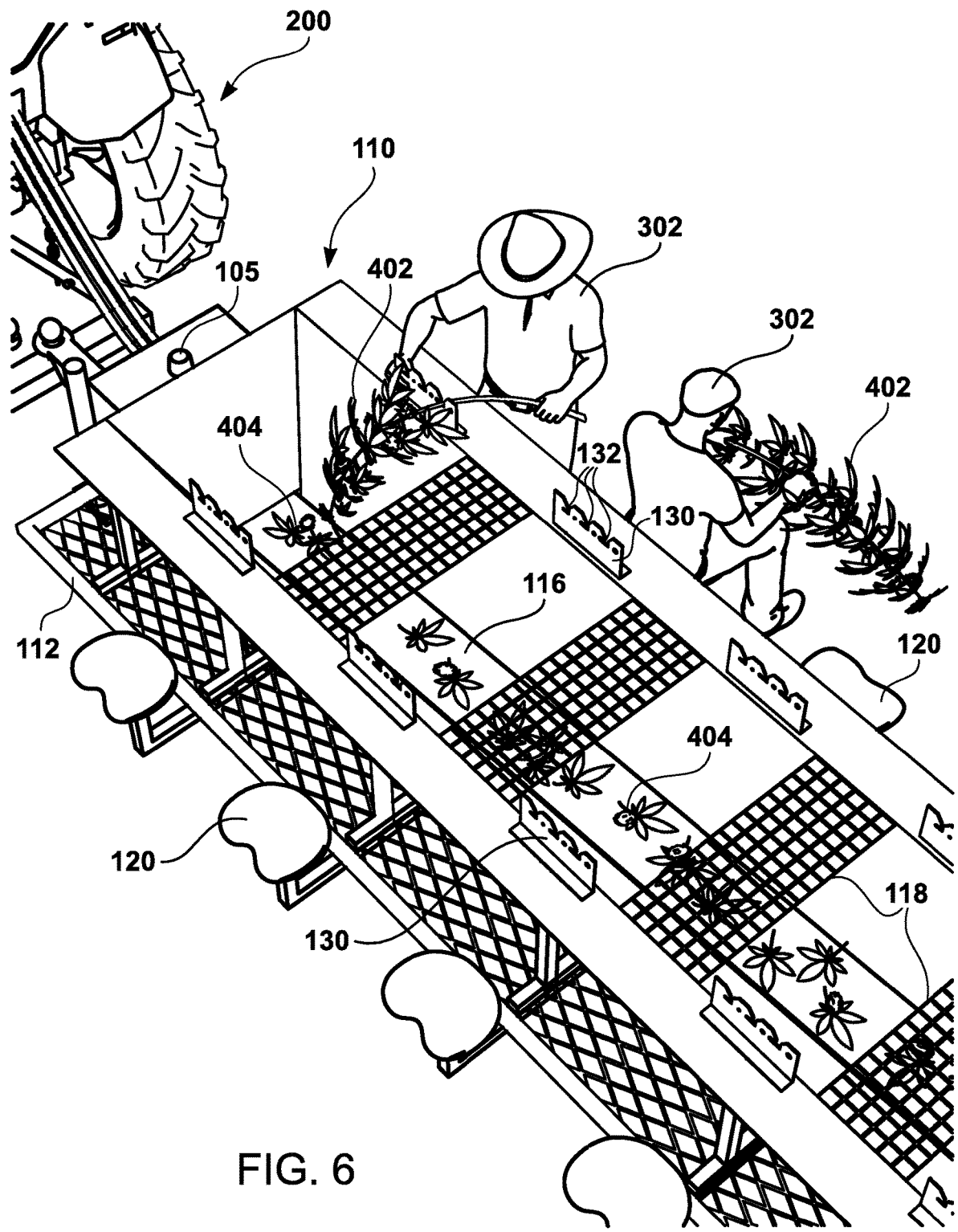
FIG. 6 illustrates the trimmed cannabis plant portion, which may include the buds and leaves without the stalk, being positioned on the conveyer belt.
Figure 7:
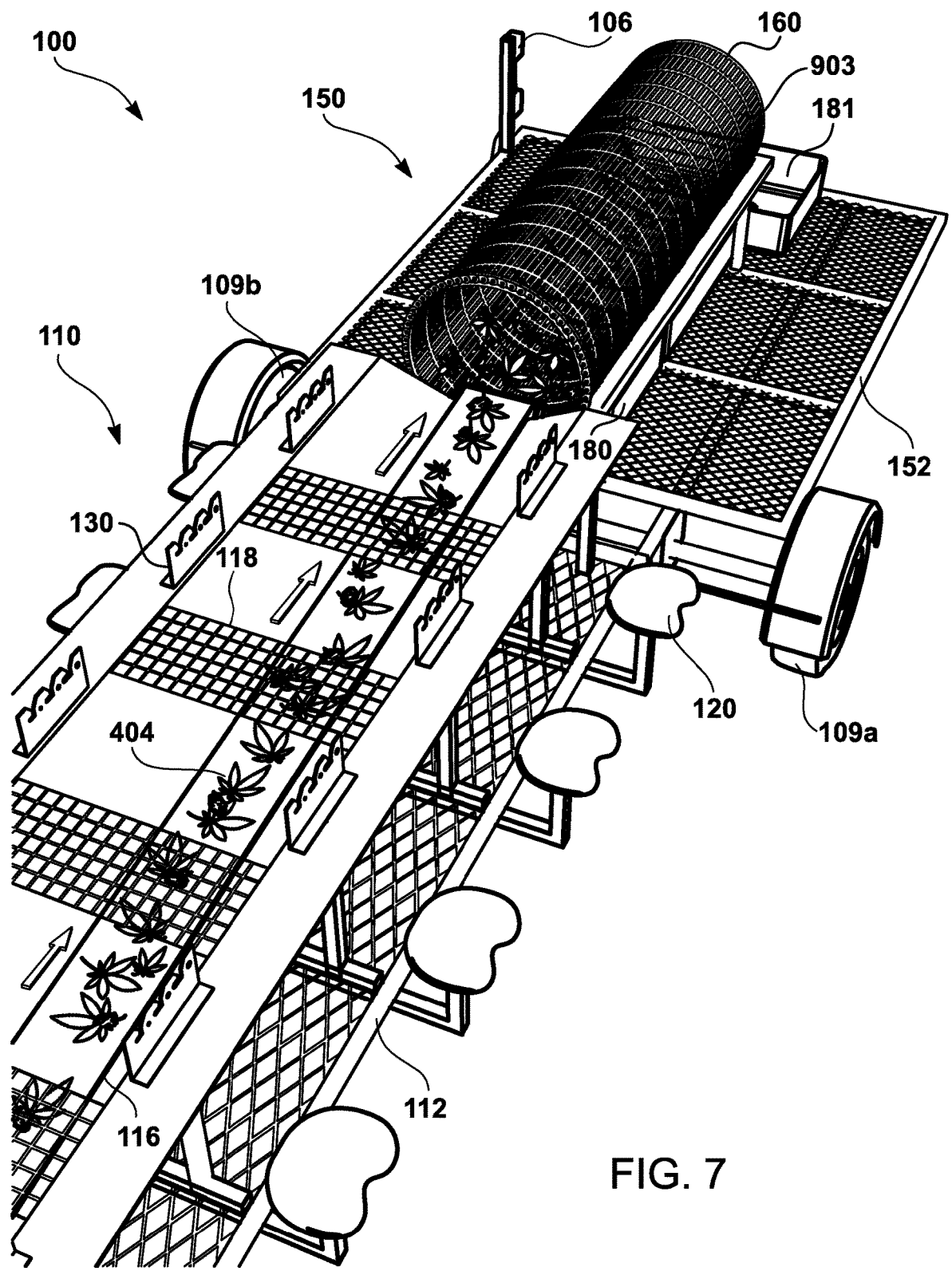
FIG. 7 illustrates the conveyer belt moving the trimmed cannabis plant portions toward the tumbler.

FIG. 3 illustrates the tractor 200, illustrated in FIG. 2, moving in conjunction with the harvesting trailer apparatus 100 through a harvesting environment 301 (e.g., a field of cannabis plants). For instance, the tractor 200 may follow a human harvester 300 that pulls a plurality of cannabis plants 402 from a cannabis crop 400. Subsequently, as illustrated in FIG. 4, a plurality of human harvesters 302 may be positioned on the seats 120 to pick up the cannabis plants 402 that were pulled by the human harvester 300 in front of the tractor 200. Furthermore, as illustrated in FIG. 5, the human harvesters 302 may pull the cannabis plants 402 through the branch trimming device 130 to effectively pull off the branches. As illustrated in FIG. 6, the trimmed cannabis plant portion 404, which may include the buds and leaves without the stalk, may be positioned on the conveyer belt 116. The conveyer belt 116, as illustrated in FIG. 7, moves the trimmed cannabis plant portions 404 toward the tumbler 160.

Figure 8:
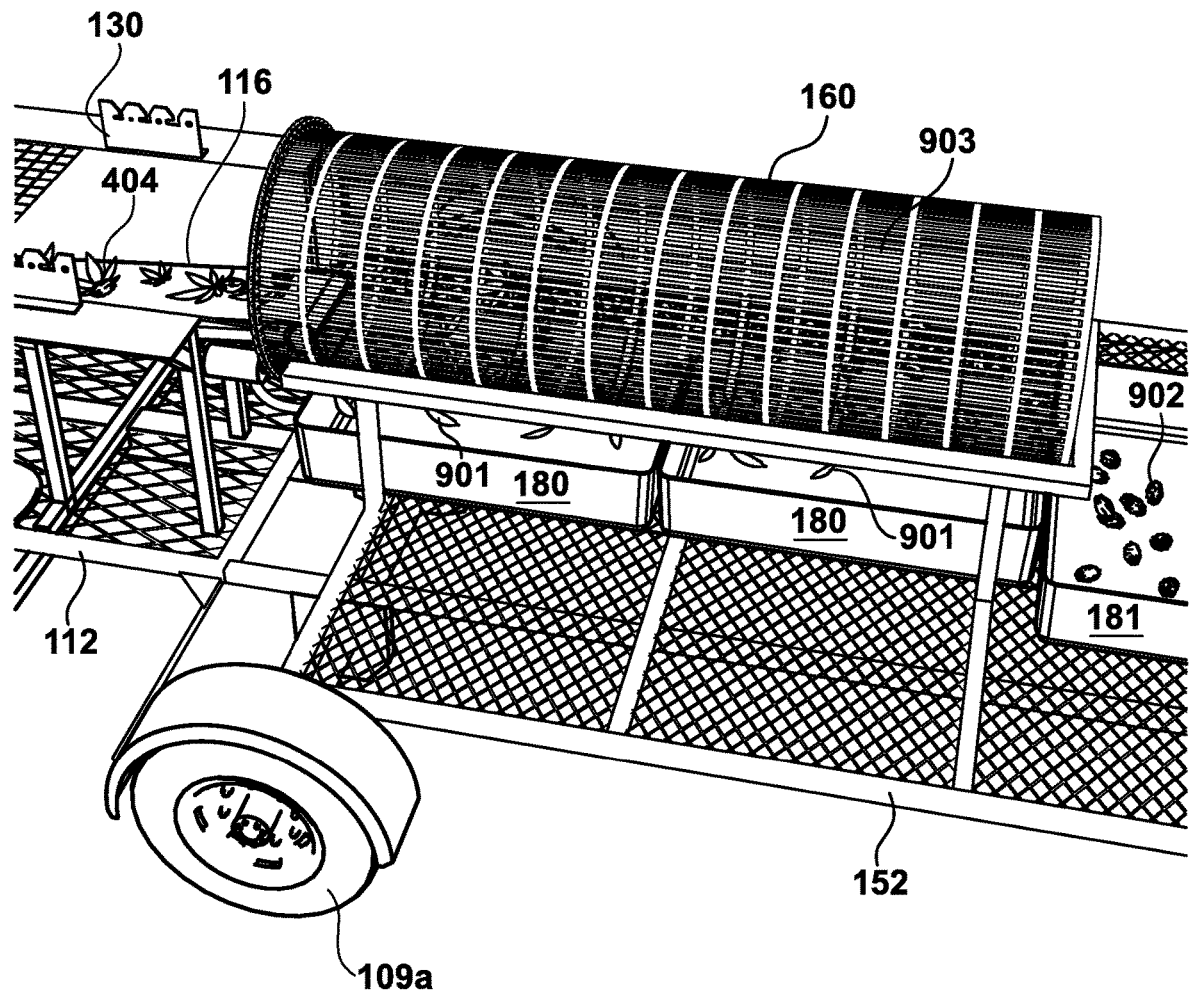
FIG. 8 illustrates the tumbler separating the leaves from the buds.
Figure 9:
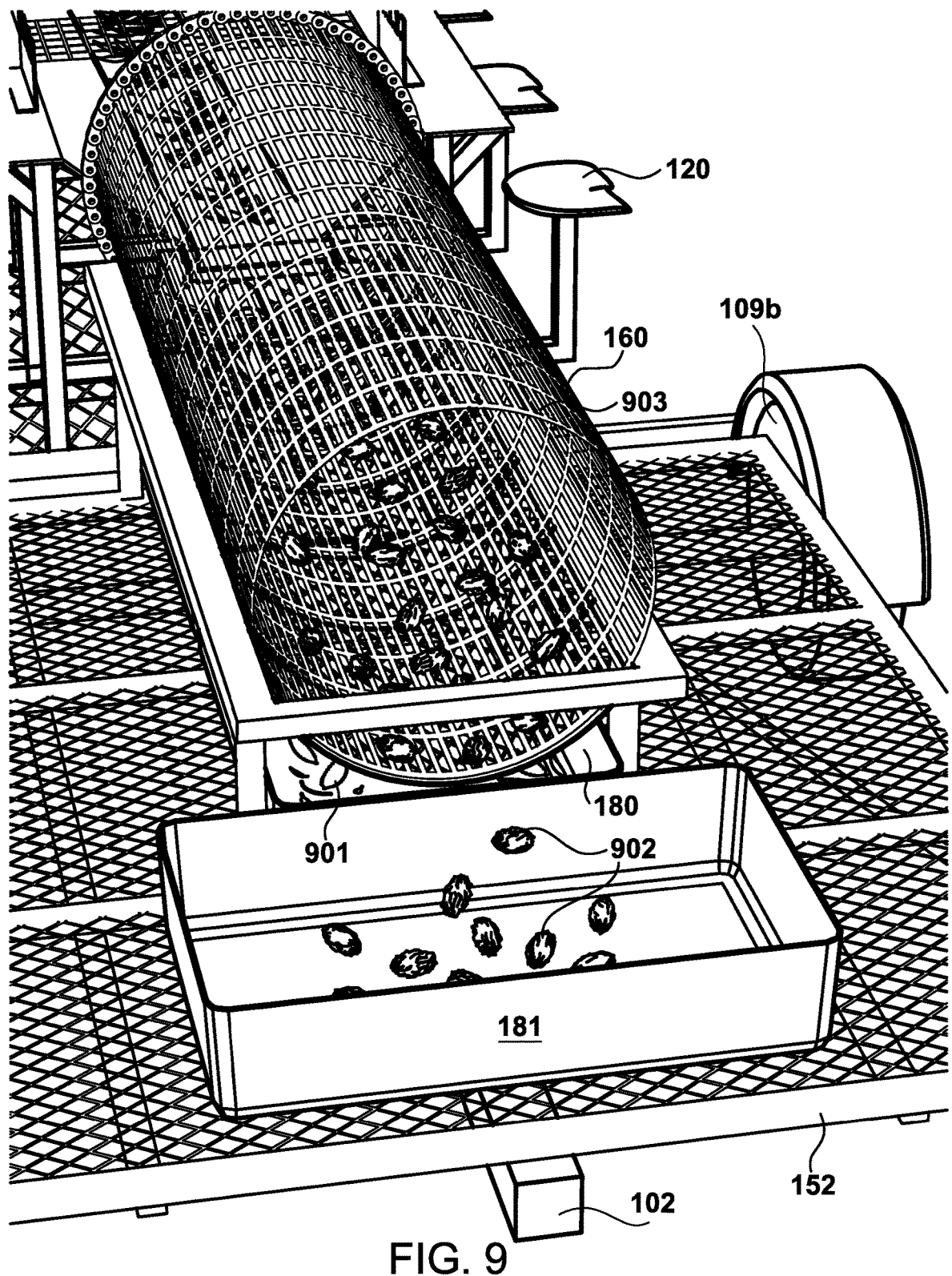
FIG. 9 illustrates the buds passing through a rear opening of the tumbler into the bud storage container.

FIG. 8 illustrates the tumbler 160 separating the leaves 901 from the buds 902. In particular, the tumbler 160 rotates with respect to the fixed cutting device 158 to trim the leaves 901 off, thereby leaving the buds 902 in the tumbler 160. The leaves 901 may fall through the one or more openings 903 (e.g., slits) in the tumbler 160 into the leave storage container 180. In particular, the openings may be sized to allow the trimmed leaves and/or branches to pass through a bottom portion of the tumbler 160; conversely, the openings may be sized to prevent the buds 902 from passing through the bottom portion of the tumbler 160. Additionally, FIG. 9 illustrates the buds 902 passing through a rear opening of the tumbler 160 into the bud storage container 181.

Figure 10:
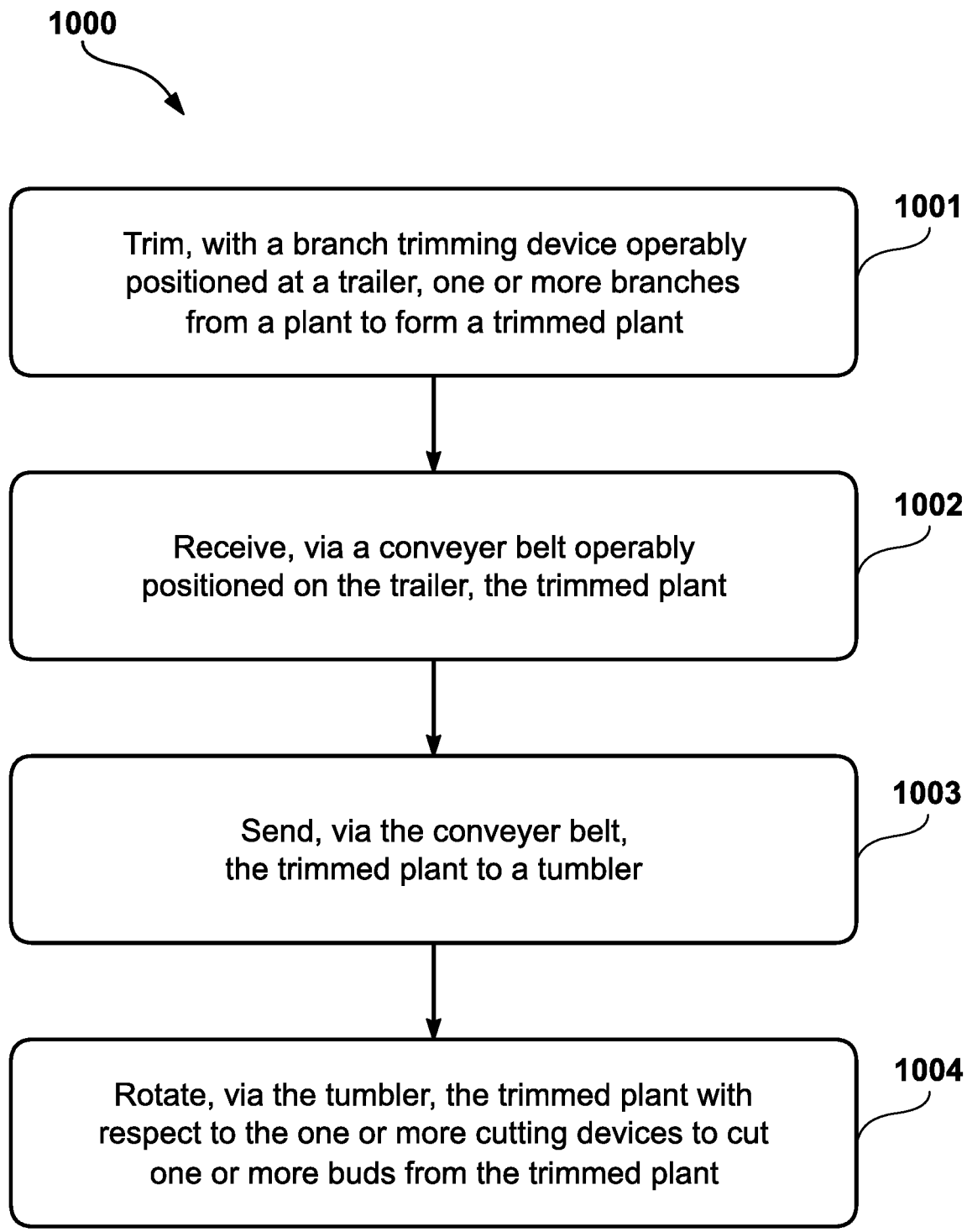
FIG. 10 illustrates a process that may be utilized by the harvesting trailer apparatus, illustrated in FIGS. 1A-9, to separate buds and leaves from cannabis plants.

Finally, FIG. 10 illustrates a process 1000 that may be utilized by the harvesting trailer apparatus 100, illustrated in FIGS. 1A-19, to separate buds 902 and leaves 901 from cannabis plants 402. In particular, at a process block 1001, the process 1000 trims, with a branch trimming device 130 operably positioned at a trailer, one or more branches from a plant to form a trimmed plant. The trailer has one or more wheels 109a and 109b, and a connector that connects the trailer to an automotive machine that mobilizes the trailer from a first position to a second position within a field of one or more plants. Additionally, at a process block 1002, the process 1000 receives, via a conveyer belt 116 operably positioned on the trailer, the trimmed plant. Furthermore, at a process block 1003, the process 1100 sends, via the conveyer belt 116, the trimmed plant to a tumbler 160. At a process block 1004, the process 1000 rotates, via the tumbler 160, the trimmed plant with respect to the one or more cutting devices 158 to cut the one or more buds 902 from the trimmed plant into. The bottom portion of the tumbler is positioned in proximity to the one or more cutting devices 158.

It is understood that the apparatuses and processes described herein may also be applied in other types of apparatuses and processes. Those skilled in the art will appreciate that the various adaptations and modifications of the embodiments of the apparatuses and processes described herein may be configured without departing from the scope and spirit of the present apparatuses and processes. Therefore, it is to be understood that, within the scope of the appended claims, the present apparatuses and processes may be practiced other than as specifically described herein.

I claim:

1. An apparatus comprising:
   a trailer having one or more wheels and a connector that connects the trailer to an automotive machine that mobilizes the trailer from a first position to a second position within a field of one or more plants;
   one or more seats positioned on the trailer;
   a branch trimming device operably positioned on the trailer;
   a conveyer belt operably positioned on the trailer, the conveyer belt receiving a trimmed plant that has one or more branches trimmed off by the branch trimming device, wherein the branch trimming device surrounds a receiving area for the trimmed plant onto which the trimmed plant is received by the conveyer belt;
   one more cutting devices; and
   a tumbler that receives the trimmed plant from the conveyer belt and rotates with respect to the one or more cutting devices to cut the one or more buds from the trimmed plant, wherein a bottom portion of the tumbler is positioned in proximity to the one or more cutting devices.

2. The apparatus of claim 1, wherein the branch trimming device is positioned above the one or more seats.

3. The apparatus of claim 1, further comprising a first motor that operates the conveyer belt.

4. The apparatus of claim 3, further comprising a second motor that rotates the tumbler.

5. The apparatus of claim 1, wherein the tumbler is a cylindrical drum.

6. The apparatus of claim 5, wherein the cylindrical drum has one or more openings that are sized to allow the trimmed branches to pass through a bottom portion of the cylindrical drum, the one or more openings also being sized to prevent the one or more buds from passing through the bottom portion of the cylindrical drum.

7. The apparatus of claim 6, wherein the apparatus has a storage compartment positioned beneath the cylindrical drum, the storage compartment receiving and storing the trimmed branches after passage through the bottom portion of the cylindrical drum.

8. The apparatus of claim 5, wherein the cylindrical drum has a rear opening that is sized to allow the one or more buds to pass through a rear portion of the cylindrical drum.

9. The apparatus of claim 8, wherein the apparatus has a storage compartment positioned in proximity to the rear portion of the cylindrical drum, the storage compartment receiving and storing the one or more buds after passage through the rear portion of the cylindrical drum.

10. The apparatus of claim 5, further comprising a cylindrical drum cover that partially covers the cylindrical drum, the cylindrical drum cover covering a top portion of the cylindrical drum without covering a bottom portion of the cylindrical drum.

11. The apparatus of claim 1, wherein the branch trimming device comprises one or more wedges through which the one or more branches are pulled from the trimmed plant.

* * * * *